US011026747B2

(12) United States Patent
Altmann et al.

(10) Patent No.: US 11,026,747 B2
(45) Date of Patent: Jun. 8, 2021

(54) ENDOSCOPIC VIEW OF INVASIVE PROCEDURES IN NARROW PASSAGES

(71) Applicant: Biosense Webster (Israel) Ltd., Yokneam (IL)

(72) Inventors: Andres Claudio Altmann, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 522 days.

(21) Appl. No.: 15/907,739

(22) Filed: Feb. 28, 2018

(65) Prior Publication Data
US 2018/0303550 A1    Oct. 25, 2018

Related U.S. Application Data

(60) Provisional application No. 62/489,953, filed on Apr. 25, 2017.

(51) Int. Cl.
*A61B 5/00* (2006.01)
*A61B 34/10* (2016.01)
(Continued)

(52) U.S. Cl.
CPC .............. *A61B 34/10* (2016.02); *A61B 5/062* (2013.01); *A61B 5/064* (2013.01); *A61B 5/6803* (2013.01);
(Continued)

(58) Field of Classification Search
CPC ......... A61B 34/10; A61B 34/20; A61B 5/064; A61B 5/6814; A61B 6/032; A61B 5/6803;
(Continued)

(56) References Cited

U.S. PATENT DOCUMENTS

2006/0004286 A1*  1/2006  Chang .................... A61B 90/16
                                                                600/435
2010/0076305 A1    3/2010  Maier-Hein et al.
(Continued)

FOREIGN PATENT DOCUMENTS

WO    WO 2005/000139    1/2005

OTHER PUBLICATIONS

European Search Report dated Sep. 28, 2018 from corresponding European Patent Application No. 18168946.4.
(Continued)

*Primary Examiner* — Joel Lamprecht
(74) *Attorney, Agent, or Firm* — Frost Brown Todd LLC

(57) ABSTRACT

A method for visualization includes registering, within a common frame of reference, a position sensing system and a three-dimensional (3D) computerized tomography (CT) image of at least a part of a body of a patient. A location and orientation of at least one virtual camera are specified within the common frame of reference. Coordinates of a medical tool moving within a passage in the body are tracked using the position sensing system. A virtual endoscopic image, based on the 3D CT image, of the passage in the body is rendered and displayed from the specified location and orientation, including an animated representation of the medical tool positioned in the virtual endoscopic image in accordance with the tracked coordinates.

22 Claims, 4 Drawing Sheets

(51) Int. Cl.
*A61B 6/03* (2006.01)
*A61B 5/06* (2006.01)
*A61B 17/24* (2006.01)
*A61B 34/20* (2016.01)
*A61M 25/09* (2006.01)
*A61B 90/00* (2016.01)
*A61B 1/00* (2006.01)

(52) U.S. Cl.
CPC ............ *A61B 5/6814* (2013.01); *A61B 6/032* (2013.01); *A61B 17/24* (2013.01); *A61B 34/20* (2016.02); *A61B 1/00009* (2013.01); *A61B 2034/105* (2016.02); *A61B 2034/2051* (2016.02); *A61B 2034/2065* (2016.02); *A61B 2034/2072* (2016.02); *A61B 2090/364* (2016.02); *A61B 2562/0223* (2013.01); *A61M 25/09* (2013.01)

(58) Field of Classification Search
CPC ... A61B 5/062; A61B 17/24; A61B 2090/364; A61B 1/00009; A61B 2034/2072; A61B 2034/2051; A61B 2034/105; A61B 2034/2065; A61B 2562/0223; A61M 25/09
See application file for complete search history.

(56) References Cited

U.S. PATENT DOCUMENTS

| | | | |
|---|---|---|---|
| 2013/0018255 | A1 | 1/2013 | Kitamura et al. |
| 2016/0007842 | A1 | 1/2016 | Govari et al. |
| 2016/0008083 | A1 | 1/2016 | Kesten et al. |
| 2016/0270863 | A1* | 9/2016 | Makower .............. A61M 29/02 |
| 2017/0020411 | A1 | 1/2017 | Gliner et al. |

OTHER PUBLICATIONS

U.S. Appl. No. 15/674,380, filed Aug. 10, 2017.
European Communication dated Oct. 13, 2020 for Application No. 18168946.4, 5 pages.

* cited by examiner

ENDOSCOPIC VIEW OF INVASIVE PROCEDURES IN NARROW PASSAGES

CROSS-REFERENCE TO RELATED APPLICATION

This application claims the benefit of U.S. Provisional Patent Application 62/489,953, filed Apr. 25, 2017, which is incorporated herein by reference.

FIELD OF THE INVENTION

The present invention relates generally to medical imaging, and particularly to methods and systems for visualization of invasive medical procedures.

BACKGROUND

In image-guided surgery (IGS), a medical practitioner uses instruments that are tracked in real time within the body, so that positions and/or orientations of the instruments can be presented on images of a patient's anatomy during the surgical procedure. In many IGS scenarios an image of the patient is prepared in one modality, such as magnetic resonance imaging (MRI) or computerized tomography (CT), and the instrument tracking uses a different modality, such as electromagnetic tracking. In order for the tracking to be effective, frames of reference of the two modalities have to be registered with each other.

Various methods are known in the art for registering a CT image with a tracking system. For example, U.S. Patent Application Publication 2017/0020411, issued as U.S. Pat. No. 10,638,954 on May 5, 2020, whose disclosure is incorporated herein by reference, describes apparatus and methods in which a processor receives a tomographic image of a subject and registers the tomographic image in the coordinate frame of a magnetic tracking system using the positions of valid registration points.

SUMMARY

Embodiments of the present invention that are described hereinbelow provide improved systems and methods for visualization of a medical tool within narrow body passages, such as the nasal sinuses.

There is therefore provided, in accordance with an embodiment of the invention, a method for visualization, which includes registering, within a common frame of reference, a position sensing system and a three-dimensional (3D) computerized tomography (CT) image of at least a part of a body of a patient. A location and orientation of at least one virtual camera within the common frame of reference are specified. Coordinates of a medical tool moving within a passage in the body are tracked using the position sensing system. A virtual endoscopic image, based on the 3D CT image, of the passage in the body is rendered and displayed from the specified location and orientation, including an animated representation of the medical tool positioned in the virtual endoscopic image in accordance with the tracked coordinates.

In a disclosed embodiment, the part of the body includes a head of the patient, and the passage includes a nasal passage, and the medical tool includes a guidewire, which is inserted into the nasal passage.

In some embodiments, the position sensing system includes an electromagnetic tracking system, which includes one or more magnetic field generators positioned around the part of the body and a magnetic field sensor at a distal end of the medical tool. In a disclosed embodiment, the one or more magnetic field generators mounted on a frame that is fixed to the part of the body, and registering the position sensing system and the 3D CT image includes formulating a first calibration of the electromagnetic tracking system relative to the frame, formulating a second calibration of the frame within the CT image, and combining the first and second calibrations to register the distal end of the tool in the common frame of reference.

In one embodiment, specifying the location and orientation of the at least one virtual camera includes receiving an input from an operator indicating the location and orientation relative to the CT image.

Additionally or alternatively, specifying the location and orientation of the at least one virtual camera includes positioning multiple virtual cameras at different, respective locations along a route of the medical tool through the passage. In one embodiment, rendering and displaying the virtual endoscopic image includes simultaneously rendering and displaying multiple virtual endoscopic images from different viewpoints corresponding to the different respective locations of the virtual cameras. Further additionally or alternatively, rendering and displaying the virtual endoscopic image includes beginning to render and display the virtual endoscopic image only when the medical tool approaches the specified location.

In some embodiments, rendering and displaying the virtual endoscopic image includes changing a viewing characteristic of the virtual endoscopic image responsively to a movement of the medical tool within the passage as indicated by the tracked coordinates. In a disclosed embodiment, changing the viewing characteristic includes changing at least one of the location and the orientation of the at least one virtual camera so as to keep the medical tool in a field of view of the at least one virtual camera as the medical tool moves through the passage.

In another embodiment, specifying the location and orientation of the at least one virtual camera includes positioning a virtual camera in a chamber having an opening that is to be accessed by the medical tool via the passage in the body, and rendering and displaying the virtual endoscopic image includes visualizing the medical tool in the passage through the opening.

There is also provided, in accordance with an embodiment of the invention, medical apparatus, including a medical tool, which is configured to move within a passage in a body of a patient, and a position sensing system, which is configured to track coordinates of the medical tool within the body. A processor is configured to register the position sensing system and a three-dimensional (3D) computerized tomography (CT) image of at least a part of the body within a common frame of reference, to identify a location and orientation of at least one virtual camera within the common frame of reference, and to render and display on a display screen a virtual endoscopic image, based on the 3D CT image, of the passage in the body from the specified location and orientation including an animated representation of the medical tool positioned in the virtual endoscopic image in accordance with the tracked coordinates.

The present invention will be more fully understood from the following detailed description of the embodiments thereof, taken together with the drawings in which:

DETAILED DESCRIPTION OF EMBODIMENTS

Figure 1:
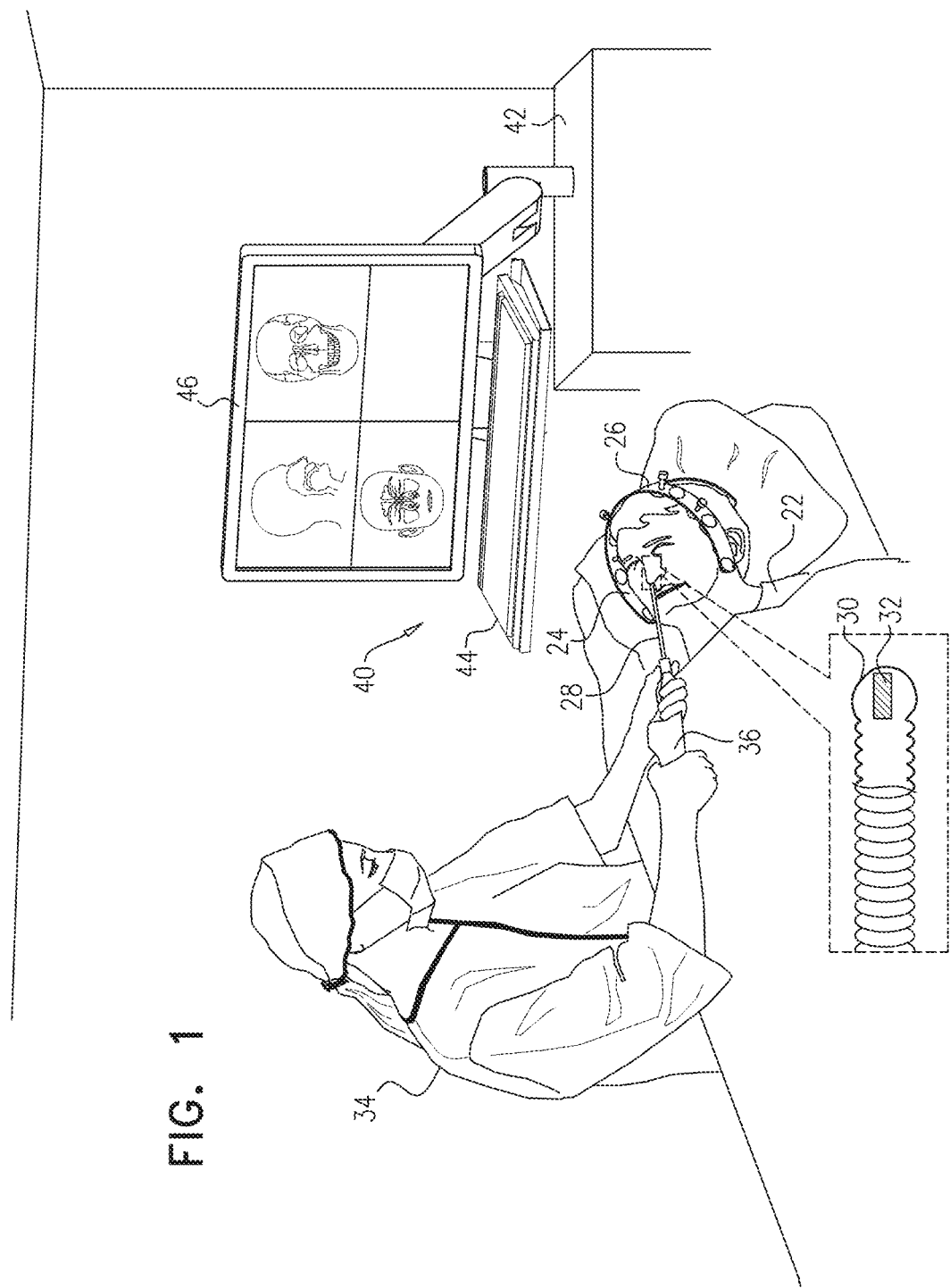
FIG. 1 is a schematic illustration of a surgery system for operation on the nasal sinuses, according to an embodiment of the present invention.

During medical procedures within the nasal passages, such as sinuplasty operations, it is impossible to directly visualize what is happening without insertion of an endoscope into the sinuses. Insertion of an endoscope is problematic, however, because of the tight spaces involved, as well as the extra cost of the endoscope. Furthermore, endoscopes for use in the nasal passages are typically rigid instruments, which cannot make turns or provide views from sinus cavities back toward the sinus opening.

Embodiments of the present invention that are described herein address this problem by generating virtual endoscopic views of the procedure, as would be seen by an actual endoscope positioned at a selected location within the nasal passages, or even by multiple endoscopes at different, respective locations. These virtual endoscope views may be used, for example, in visualizing the location and orientation of a guidewire relative to the anatomy, as well as other tools, such as a suction tool or a shaving tool (debrider). Furthermore, although the embodiments disclosed hereinbelow are directed specifically to visualization within the nasal passages, the principles of the present invention may similarly be applied within other spaces in the body, particularly in narrow passages in which actual optical endoscopy is unavailable or difficult to use.

Prior to the medical procedure, a CT image of the patient's head, including the sinuses, is acquired, and a tracking system, such as an electromagnetic tracking system, is registered with the CT image. A position sensor is attached to the distal end of the guidewire or other tool, and the distal end is thus tracked, in location and orientation, relative to the registered CT image, as it is inserted into the sinuses.

The CT image of the head is processed in order to generate and display images of the 3D volume of the nasal passages. Inside this 3D volume, an operator of the imaging system, such as a surgeon performing a sinuplasty procedure, can place multiple virtual cameras, for example by pointing to the desired positions and viewing angles on the displayed CT images. The operator is thus able to position an "endoscope," on the basis of the planned approach route of a tool, in areas of the nasal passages where the actual tool has not yet arrived. For example, the operator can place a virtual camera within the target cavity itself (such as in a sinus cavity), looking back toward the tiny opening of this cavity (the sinus opening), and can then use this view in visualizing and steering the flexible guidewire through the opening. The resulting virtual endoscopic images thus enable the operator to view and control the entry of the tool into these areas with enhanced confidence.

The virtual cameras may be stationary, or they may move so as to keep the distal end of the tool in view as the operator maneuvers it through the nasal passages. Additionally or alternatively, the system itself may automatically position one or more virtual cameras so as to view and track the distal end of the tool. Multiple virtual views of the tool can be generated simultaneously and can be displayed on a viewing screen, instead of or in addition to conventional CT slice views. Further additionally or alternatively, the imaging system can generate virtual endoscopic views as would be seen from the distal tip of the tool itself; but the inventors have found that views of the tool provided by virtual cameras at locations that are spaced away from the tool can provide more intuitive guidance.

FIG. 1 is a schematic illustration of a nasal sinus surgery system 20, according to an embodiment of the present invention. System 20 is used in the present example in a surgical procedure within a nasal sinus of a patient 22.

For the actual procedure, a set of one or more magnetic field generators 24 is fixed to or around the head of the patient, for example by incorporating the generators into a frame 26, which is clamped to the patient's head. The field generators create magnetic fields, which are detected by a position sensor 32, such as a suitable coil, at a distal end 30 of a tool 28, such as a guidewire. When tool 28 is inserted into the nasal sinuses of patient 22, the signals output by the position sensor are processed by a system processor 40 in order to find location and orientation coordinates of the distal end of the probe. An electromagnetic position tracking system of this sort is described, for example, in U.S. Patent Application Publication 2016/0007842, issued as U.S. Pat. No. 10,772,489 on Sep. 15, 2020, whose disclosure is incorporated herein by reference. In addition, the Carto® system produced by Biosense Webster, of Diamond Bar, Calif., uses a tracking system similar to that described herein for finding the location and orientation of a coil in a region irradiated by magnetic fields. Alternatively, although electromagnetic tracking is particularly advantageous in terms of being both highly accurate and well suited to operation within the human body, the principles of the present invention may be applied using other tracking technologies that are known in the art.

Elements of system 20, including field generators 24, are controlled by system processor 40, comprising a programmable processing unit communicating with one or more memories. Processor 40 is contained in a console 42, which comprises operating controls 44 that typically include a keypad and/or a pointing device such as a mouse or trackball. Console 52 also connects to other elements of system 20, such as a proximal end 36 of tool 28. An operator 34, such as a physician, uses the operating controls to interact with the processor while performing the procedure. Processor 40 present images and other results produced by system 20 on a screen 46.

Processor 40 typically comprises a programmable microprocessor, having suitable interfaces and software, stored in a memory in console 42, to receive input signals from the components of system 20 and to output control signals in order to operate the system. The software may be downloaded to processor 40 in electronic form, over a network, for example, or it may, alternatively or additionally, be provided and/or stored on non-transitory tangible computer-readable media, such as magnetic, optical, or electronic memory.

Processor 40 uses the software, inter alia, to operate and calibrate magnetic field generators 24. The generators are operated so as to transmit alternating magnetic fields at different frequencies into a region in proximity to frame 26. Prior to being placed on the patient, the generators in the frame may be calibrated by positioning a probe with a sensing coil, such as sensor 32, in the region in known locations and orientations relative to the frame. Signals are induced in the coil by the alternating magnetic fields, and the processor acquires and records the signals. The processor then formulates a calibration relationship between the locations and orientations of the coil, and the recorded signals for these locations and orientations.

Once the calibration relationship has been formulated, frame 26 may be placed on the head of patient 22. After placement, the frame is fixed in position and registered with external features of the patient's head, for example by imaging the patient's head with the attached frame from a number of different angles. The frame registration also registers magnetic field generators 24 with the patient's external features. Alternatively or additionally, the registration may include placing a probe with a sensing coil, such as sensor 32, in one or more known locations and orientations with respect to the external features of the patient, as well as with frame 26, and measuring the signals output by the coil.

Figure 2:
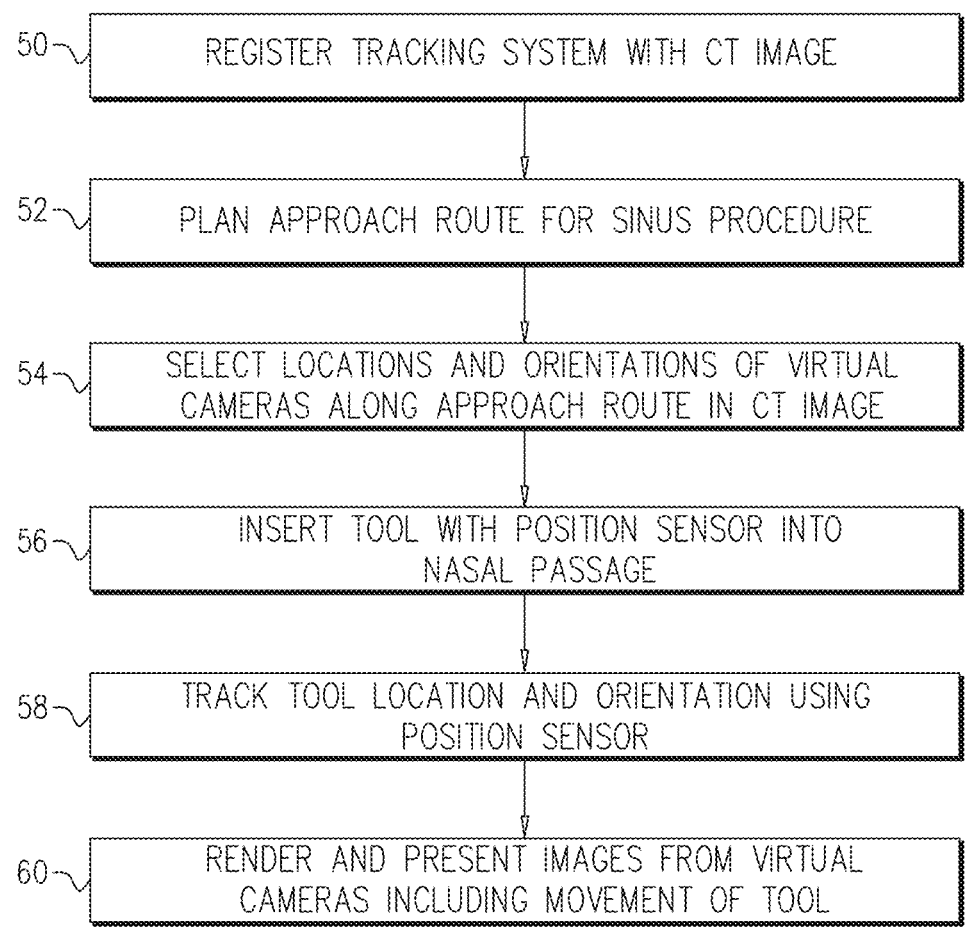
FIG. 2 is a flow chart that schematically illustrates a method for visualization of a medical tool within nasal passages, in accordance with an embodiment of the invention.

FIG. 2 is a flow chart that schematically illustrates a method for visualization of a medical tool within the nasal passages, in accordance with an embodiment of the invention. The method is described, for the sake of convenience, with reference to system 20 (FIG. 1) and tool 28, but it may alternatively be carried out in other system environments and other sorts of medical procedures.

As an initial registration step 50, a CT image is acquired of the head of patient 22, and the frame of reference of the tracking system defined by field generators 24 is registered with the CT image. Thus, the tracking system coordinates defined by frame 26 and field generators 24 share the same frame of reference with the CT image coordinates. The calibration can be carried out, for example, as described above by capturing one or more images of the patient's head (possibly including the CT image itself) with frame 26 already fixed to the head. Processor 40 processes these images to identify the location and orientation of frame 26 in the CT frame of reference, and combines this information with the calibration of the electromagnetic tracking system to register all the elements of system 20 in the same frame of reference.

Alternatively or additionally, any other suitable registration technique may be used for this purpose, such as the method described in the above-mentioned U.S. Patent Application Publication 2017/0020411, issued as U.S. Pat. No. 10,638,954 on May 5, 2020, or the techniques described in U.S. patent application Ser. No. 15/674,380, filed Aug. 10, 2017, published as U.S. Pub. No. 2019/0046272 on Feb. 14, 2019, whose disclosure is likewise incorporated herein by reference. As described in this latter patent application, for example, processor 40 may analyze the CT image at step 50 to identify respective locations of the patient's eyes in the image, thus defining a line segment joining these respective locations. In addition, processor 40 identifies a voxel subset in the CT that overlies bony sections of the head, along a second line segment parallel to the first line segment and a third line segment perpendicular to the first line segment. Operator 34 positions a probe in proximity to the bony sections and thus measures positions on the surface of the head overlying the bony sections. Processor 40 computes the correspondence between these measured positions and the voxel subset in the CT image and thus registers the magnetic tracking system with the CT image.

Processor 40 presents CT images of the patient's nasal passages to operator 34, at an approach planning step. The images can be presented as 2D slices and/or as reconstructed pseudo-3D volumes, which are processed and segmented, as is known in the CT art, so that the operator can readily distinguish between solid tissue and open, transparent spaces, such as the sinuses. Operator 34 uses these images both to plan the approach route of tool 28 through the sinuses, at step 52, and to select the locations and orientations of virtual cameras to be placed along the approach route, at a location selection step 54.

For this latter purpose, processor 40 may present the images on screen 46, and operator 34 may then mark the desired camera locations and orientations using a pointing device or touch interface. As noted earlier, the operator can decide whether the virtual cameras (and hence their points of view) should be stationary, or whether they should change their viewing characteristics, such as location, orientation and/or zoom angle, as tool 28 moves through the nasal passages (as indicated by the position coordinates). For example, the operator may instruct processor 40 that a given virtual camera is to track the motion of distal end 30 of tool 28 as it progresses along the approach route and performs the planned procedure. Alternatively, the operator can set the position and orientation of a virtual camera in advance, while instructing processor 40 to actually enable the virtual camera (i.e., begin to render and display virtual endoscopic images from the camera viewpoint) only when tool 28 approaches the corresponding anatomical region.

Having "activated" a virtual camera or cameras in this fashion, operator 54 inserts tool 28 through the patient's nostril and into the nasal passages along the desired route, at a tool insertion step 56. Position sensor 32 at distal end 30 of tool 28 outputs signals in response to the magnetic fields produced by field generators 24. Processor 40 computes location and orientation coordinates of the distal end of the tool based on these signals, and locates the tool relative to the CT image using the registration transformation found at step 50, at a tool tracking step 58.

Based on the tool location and orientation and the pre-acquired CT data, processor 40 renders images as they would be captured by the virtual cameras and presents the images on screen 46, at a rendering step 60. The image rendered by any given virtual camera is a projection of the portion of the 3D volume of the nasal passages that would be visible from the camera location onto the virtual image plane of the camera. When the location coordinates of distal end 30 of tool 28 indicate that it is within the field of view of the virtual camera, processor 40 superimposes an animated picture of the tool in the appropriate location and orientation on the projected 3D volume. Processor 40 may present a single image on screen 46, or it may present multiple images corresponding to different camera locations and fields of view. As noted earlier, the field of view of a given camera may change during the procedure either under operator control or automatically, for example to keep the tool in view as it advances along the route of the procedure.

Figure 3:
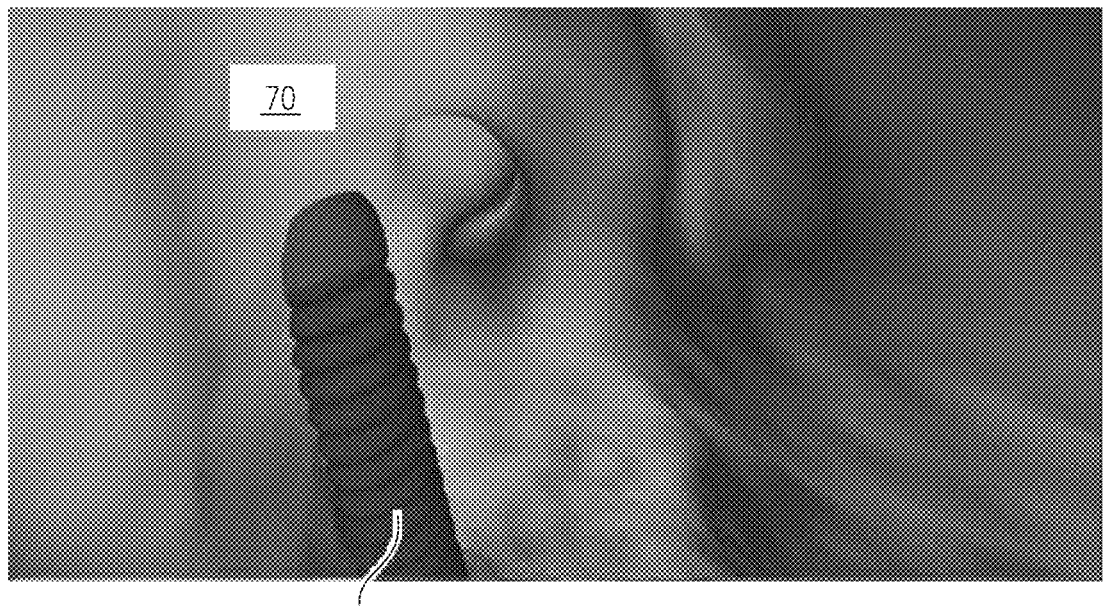
FIGS. 3-5 are schematic representations of virtual endoscopic images showing the distal end of a tool as it moves through the nasal passages, in accordance with an embodiment of the invention.
Figure 4:
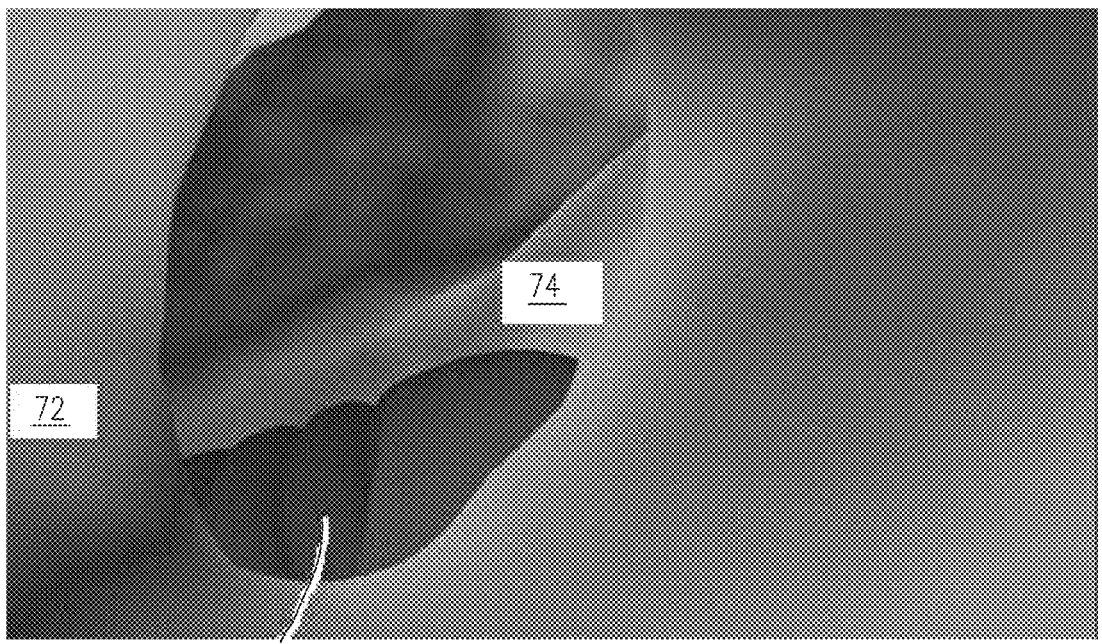
Figure 5:
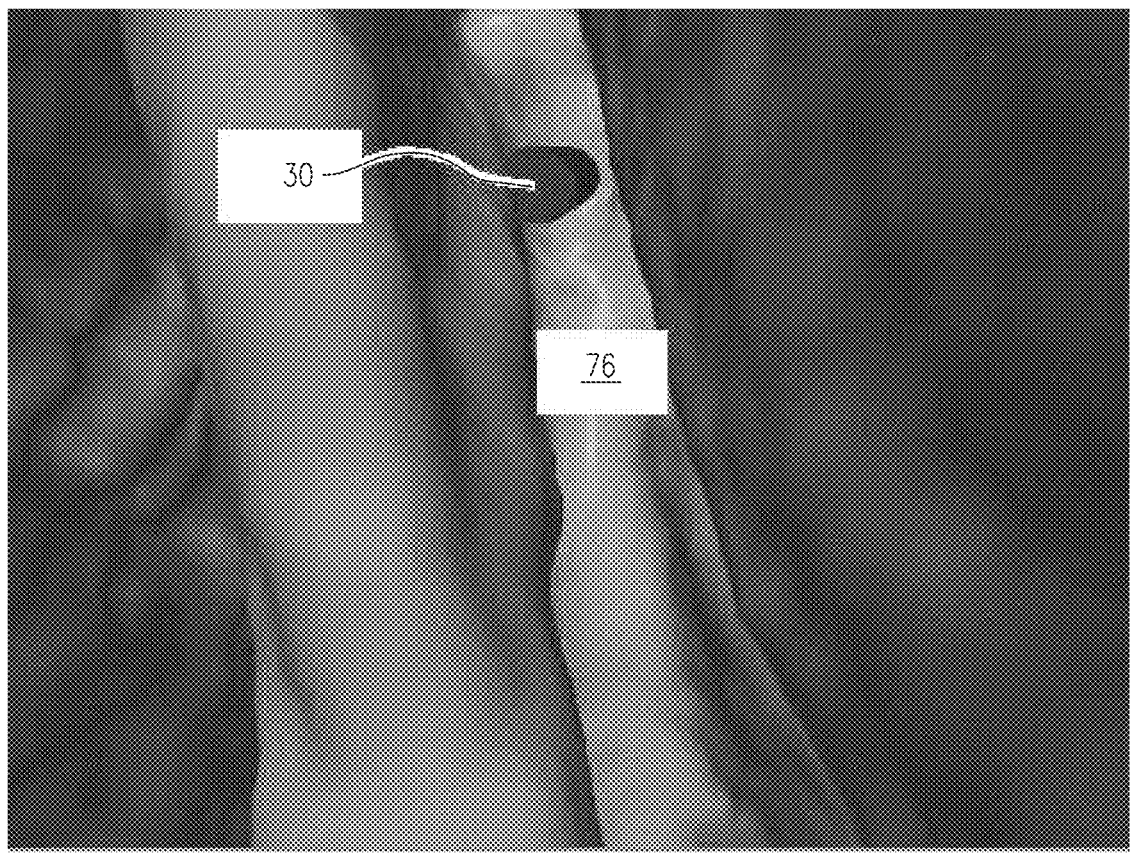

FIGS. 3-5 are schematic representations of virtual endoscopic images showing distal end 30 of tool 28 (in this case a guidewire) as it moves through the nasal passages, in accordance with an embodiment of the invention. In FIG. 3, the distal end of the guidewire is viewed by a virtual camera that is located in the same chamber 70 of the nasal passage as the current location of the guidewire. In FIG. 4, on the other hand, distal end 30 is located in a chamber 74, while the virtual camera is located in a different chamber 72 and "sees" only a small part of the guidewire that is visible through an opening in the chamber wall.

FIG. 5 shows an image generated by a virtual camera that is configured as an endoscope, which moves through nasal passage 76 behind distal end 30 of tool 28. In this view, processor 40 renders and overlays only the distal portion of the guidewire on the 3D CT image, so that the image of the surrounding tissues that is provided by the virtual endoscope is not obscured by the guidewire. As the guidewire advances through the passages, the point of view of the virtual endoscope moves along behind it.

The above images are presented only for purposes of illustration, and other sorts of images may likewise be rendered and displayed in accordance with the principles of the present invention. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for visualization, comprising:
   registering, within a common frame of reference, a position sensing system and a three-dimensional (3D) computerized tomography (CT) image of at least a part of a body of a patient;
   specifying, via user input, a performance characteristic, location, and orientation of at least one virtual camera within the common frame of references, wherein specifying the performance characteristic comprises instructing a processor to enable the at least one virtual camera to begin to render and display a virtual endoscopic image only when the medical tool approaches the specified location;
   tracking coordinates of a medical tool moving within a passage in the body using the position sensing system; and
   rendering and displaying the virtual endoscopic image, based on the 3D CT image, of the passage in the body from the specified location and orientation including an animated representation of the medical tool positioned in the virtual endoscopic image in accordance with the tracked coordinates.

2. The method according to claim 1, wherein the part of the body comprises a head of the patient, and wherein the passage comprises a nasal passage.

3. The method according to claim 2, wherein the medical tool comprises a guidewire, which is inserted into the nasal passage.

4. The method according to claim 1, wherein the position sensing system comprises an electromagnetic tracking system, which comprises one or more magnetic field generators positioned around the part of the body and a magnetic field sensor at a distal end of the medical tool.

5. The method according to claim 4, wherein the one or more magnetic field generators mounted on a frame that is fixed to the part of the body, and wherein registering the position sensing system and the 3D CT image comprises the processor:
   formulating a first calibration of the electromagnetic tracking system relative to the frame;
   formulating a second calibration of the frame within the CT image; and
   combining the first and second calibrations to register the distal end of the tool in the common frame of reference.

6. The method according to claim 1, wherein specifying the location and orientation of the at least one virtual camera comprises receiving an input from an operator indicating the location and orientation relative to the CT image.

7. The method according to claim 1, wherein specifying the location and orientation of the at least one virtual camera comprises positioning multiple virtual cameras at different, respective locations along a route of the medical tool through the passage.

8. The method according to claim 7, wherein rendering and displaying the virtual endoscopic image comprises simultaneously rendering and displaying multiple virtual endoscopic images from different viewpoints corresponding to the different respective locations of the virtual cameras.

9. The method according to claim 1, wherein rendering and displaying the virtual endoscopic image comprises changing a viewing characteristic of the virtual endoscopic image responsively to a movement of the medical tool within the passage as indicated by the tracked coordinates.

10. The method according to claim 9, wherein changing the viewing characteristic comprises changing at least one of the location and the orientation of the at least one virtual camera so as to keep the medical tool in a field of view of the at least one virtual camera as the medical tool moves through the passage.

11. The method according to claim 1, wherein specifying the location and orientation of the at least one virtual camera comprises positioning the at least one virtual camera in a chamber having an opening that is to be accessed by the medical tool via the passage in the body, and wherein rendering and displaying the virtual endoscopic image comprises visualizing the medical tool in the passage through the opening.

12. Medical apparatus, comprising:
   a medical tool, which is configured to move within a passage in a body of a patient;
   a position sensing system, which is configured to track coordinates of the medical tool within the body;
   a display screen; and
   a processor, which is configured to:
      register the position sensing system and a three-dimensional (3D) computerized tomography (CT) image of at least a part of the body within a common frame of reference,
      receive input specifying a performance characteristic, a location, and orientation of at least one virtual camera within the common frame of reference, wherein the input specifying the performance characteristic comprises an instruction to enable the at least one virtual camera to begin to render and display a virtual endoscopic image only when the medical tool approaches the specified location, and
      render and display on the display screen the virtual endoscopic image, based on the 3D CT image, of the passage in the body from the specified location and orientation including an animated representation of the medical tool positioned in the virtual endoscopic image in accordance with the tracked coordinates.

13. The apparatus according to claim 12, wherein the part of the body comprises a head of the patient, and wherein the passage comprises a nasal passage.

14. The apparatus according to claim 13, wherein the medical tool comprises a guidewire, which is inserted into the nasal passage.

15. The apparatus according to claim 12, wherein the position sensing system comprises an electromagnetic tracking system, which comprises one or more magnetic field generators positioned around the part of the body and a magnetic field sensor at a distal end of the medical tool.

16. The apparatus according to claim 15, and comprising a frame, which is fixed to the part of the body and on which the one or more magnetic field generators are mounted, wherein the processor is configured to register the position sensing system and the 3D CT image by formulating a first calibration of the electromagnetic tracking system relative to the frame, formulating a second calibration of the frame within the CT image, and combining the first and second calibrations to register the distal end of the tool in the common frame of reference.

17. The apparatus according to claim 12, wherein the processor is configured to identify the location and orientation of the last least one virtual camera by performing steps comprising receiving an input from an operator of the apparatus indicating the location and orientation of the at least one virtual camera relative to the CT image.

18. The apparatus according to claim 12, wherein the processor is configured to position multiple virtual cameras at different, respective locations along a route of the medical tool through the passage.

19. The apparatus according to claim 18, wherein the processor is configured to simultaneously render and display on the display screen multiple virtual endoscopic images from different viewpoints corresponding to the different respective locations of the virtual cameras.

20. The apparatus according to claim 12, wherein the processor is configured to change a viewing characteristic of the virtual endoscopic image responsively to a movement of the medical tool within the passage as indicated by the tracked coordinates.

21. The apparatus according to claim 20, wherein changing the viewing characteristic comprises changing at least one of the location and the orientation of the at least one virtual camera so as to keep the medical tool in a field of view of the at least one virtual camera as the medical tool moves through the passage.

22. The apparatus according to claim 12, wherein the processor is configured to position a virtual camera in a chamber having an opening that is to be accessed by the medical tool via the passage in the body, and to render and display the virtual endoscopic image so as to visualize the medical tool in the passage through the opening.

\* \* \* \* \*